US009201048B2

(12) United States Patent
Cheng et al.

(10) Patent No.: US 9,201,048 B2
(45) Date of Patent: Dec. 1, 2015

(54) SYSTEMS FOR CHARACTERIZING RESONANCE BEHAVIOR OF MAGNETOSTRICTIVE RESONATORS

(75) Inventors: Zhongyang Cheng, Auburn, AL (US); Anxue Zhang, Xi'an (CN); Kewei Zhang, Auburn, AL (US); Bryan Chin, Auburn, AL (US)

(73) Assignee: Auburn University, Auburn, AL (US)

( * ) Notice: Subject to any disclaimer, the term of this patent is extended or adjusted under 35 U.S.C. 154(b) by 828 days.

(21) Appl. No.: 13/441,572

(22) Filed: Apr. 6, 2012

(65) Prior Publication Data

US 2012/0280682 A1 Nov. 8, 2012

Related U.S. Application Data

(60) Provisional application No. 61/472,346, filed on Apr. 6, 2011.

(51) Int. Cl.
*G01N 29/30* (2006.01)
*G01N 33/02* (2006.01)
*G01N 29/24* (2006.01)

(52) U.S. Cl.
CPC ............ *G01N 29/2412* (2013.01); *G01N 29/30* (2013.01); *G01N 33/02* (2013.01)

(58) Field of Classification Search
USPC ................. 324/300–322; 250/20; 455/266; 436/526, 525; 600/407–435
See application file for complete search history.

(56) References Cited

U.S. PATENT DOCUMENTS

| 2,353,180 | A | * | 7/1944 | Muller | 455/266 |
|---|---|---|---|---|---|
| 6,397,661 | B1 | | 6/2002 | Grimes et al. | |
| 7,113,876 | B2 | | 9/2006 | Zeng et al. | |
| 7,138,238 | B2 | | 11/2006 | Vodyanoy et al. | |
| 7,267,993 | B2 | | 9/2007 | Pentrenko et al. | |
| 7,473,550 | B2 | | 1/2009 | Vodyanoy et al. | |
| 7,670,765 | B2 | | 3/2010 | Petrenko et al. | |
| 7,759,134 | B2 | * | 7/2010 | Chin et al. | 436/525 |
| 2004/0113801 | A1 | | 6/2004 | Gustafson et al. | |
| 2005/0074904 | A1 | * | 4/2005 | Chin et al. | 436/526 |
| 2008/0071487 | A1 | | 3/2008 | Zeng et al. | |
| 2009/0145239 | A1 | | 6/2009 | Girshovich et al. | |
| 2009/0284249 | A1 | | 11/2009 | Syracuse et al. | |
| 2012/0280682 | A1 | * | 11/2012 | Cheng et al. | 324/301 |
| 2014/0120524 | A1 | | 5/2014 | Chin et al. | |

OTHER PUBLICATIONS

ISA/US, International Search Report and Written Opinion for PCT/US2013/066922, Mar. 18, 2014, 10 pages.

(Continued)

*Primary Examiner* — Melissa Koval
*Assistant Examiner* — Tiffany Fetzner
(74) *Attorney, Agent, or Firm* — Barnes & Thornburg LLP (57) ABSTRACT

Illustrative embodiments of systems for characterizing resonance behavior of magnetostrictive resonators are disclosed. In one illustrative embodiment, an apparatus may comprise a first channel including one or more driving coils and one or more magnetostrictive resonators, the first channel having a first impedance; a second channel having a second impedance, the second impedance differing from the first impedance by an impedance attributable to the one or more magnetostrictive resonators; a signal source configured to apply an input signal to both the first and second channels; and a signal receiver configured to generate a combined output signal in response to output signals measured from both the first and second channels.

19 Claims, 9 Drawing Sheets

(56) References Cited

OTHER PUBLICATIONS

Zhang et al., "Development of Highly Sensitive Handheld Device for Real-Time Detection of Bacteria in Food," Proc. of SPIE vol. 7676, 2010, 12 pages.

Chai et al., "Design of a Surface-Scanning Coil Detector for Direct Bacteria Detection on Food Surfaces Using a Magnetoelastic Biosensor," J. Applied Physics, 2013, 8 pages, vol. 114,104504.

Chai et al., "A Surface-Scanning Coil Detector for Real-Time, In-Situ Detection of Bacteria on Fresh Food Surfaces," Biosensors and Bioelectronics, 2013, pp. 311-317, vol. 50.

* cited by examiner

SYSTEMS FOR CHARACTERIZING RESONANCE BEHAVIOR OF MAGNETOSTRICTIVE RESONATORS

CROSS-REFERENCE TO RELATED APPLICATIONS

This application claims priority under 35 U.S.C. §119(e) to U.S. Provisional Patent Application Ser. No. 61/472,346, filed on Apr. 6, 2011, and entitled "Technologies and Circuitries for Characterizing Behavior of Magnetostrictive/Magnetoelastic Resonator(s)," the entire disclosure of which is expressly incorporated herein by reference.

STATEMENT REGARDING FEDERALLY SPONSORED RESEARCH

This invention was made with government support under USDA-2009-34605-198055 and USDA-2005-343941-5674A, both awarded by the U.S. Department of Agriculture, and USGS-06HWGR0070, awarded by the U.S. Geological Survey. The government has certain rights in the invention.

BACKGROUND

The present disclosure relates, generally, to magnetostrictive resonators and, more particularly, to systems for characterizing the resonance behavior of magnetostrictive resonators. It will be appreciated by those of skill in the art that magnetostrictive resonators are also sometimes referred to as magnetoelastic resonators, and the present disclosure will refer to both types of devices as "magnetostrictive resonators," or simply "resonators."

Biosensor systems may be used to detect and/or measure the presence of a wide variety of biological species (e.g., pathogenic bacteria and viruses that are widely found in food, soil, and water). A typical biosensor system comprises of three parts: (1) a sensing element, (2) a sensor platform, and (3) an interrogation system. The sensing element (e.g., antibody, phage, etcetera) may react with a target species in a sample due to its biomolecular recognition properties, which results in a physical and/or chemical change in the sensing element. As the change in the sensing element is usually not observable by direct human visualization, the sensor platform is utilized to detect and/or measure this change. In other words, the sensor platform converts the physical and/or chemical change in the sensing element into an output signal (e.g., an electromagnetic signal). The interrogation system is used to measure the output signal of the sensor platform (and often performs signal amplification, processing, and display, among other operations). Such biosensor systems may offer many advantages, such as sensitivity, ease of operation, and fast detection, making biosensor systems an excellent candidate for in-the-field detection and/or monitoring.

Various types of sensor platforms have been investigated in the development of high-performance biosensor systems, such as acoustic wave devices and optical fiber devices. Among the acoustic wave devices, magnetostrictive resonators provide many advantages. For instance, one advantage of magnetostrictive resonators over other acoustic wave devices is that magnetostrictive resonators may be wirelessly interrogated. When a magnetic field is applied to a magnetostrictive resonator, the shape of the resonator will change depending on the magnetic field. If a time-varying magnetic field is applied, a vibration will be introduced in the magnetostrictive resonator. The magnetostrictive resonator then generates its own time-varying magnetic field, which may be wirelessly measured. When coupled with one or more sensing elements, a magnetostrictive resonator may operate as a mass sensor because its resonance frequency will change with a mass load. In such embodiments, the resonance frequency of the magnetostrictive resonator serves as the output signal of the sensing platform. For high-performance biosensor systems to fully utilize the advantages of magnetostrictive resonators as sensing platforms, appropriate interrogation systems are needed.

SUMMARY

According to one aspect, an apparatus may comprise a first channel including one or more coils and one or more magnetostrictive resonators, the first channel having a first impedance, a second channel having a second impedance, the second impedance differing from the first impedance by an impedance attributable to the one or more magnetostrictive resonators, a signal source configured to apply an input signal to both the first and second channels, and a signal receiver configured to generate a combined output signal in response to output signals measured from both the first and second channels.

In some embodiments, the one or more magnetostrictive resonators may comprise a plurality of magnetostrictive resonators. The one or more coils may surround a first portion of a sample and the one or more magnetostrictive resonators may be disposed in the first portion of the sample. The one or more magnetostrictive resonators may each comprise a sensing element that reacts with a target species in the sample. The second channel may include one or more coils surrounding a second portion of the sample and no magnetostrictive resonators are disposed in the second portion of the sample. The second channel may further include a linear element electrically coupled to the one or more coils of the second channel. The first channel may further include a linear element electrically coupled to the one or more coils of the first channel. The signal source may be configured to sweep the input signal over a range of frequencies including a resonance frequency of the one or more magnetostrictive resonators.

In some embodiments, the combined output signal may be a difference between the output signals measured from both the first and second channels. In other embodiments, the combined output signal may be a ratio between the output signals measured from both the first and second channels. The apparatus may further comprise a processor configured to determine a resonance behavior of the one or more magnetostrictive resonators in response to the combined output signal. The resonance behavior of the one or more magnetostrictive resonators may comprise a resonance frequency of the one or more magnetostrictive resonators. The resonance behavior of the one or more magnetostrictive resonators may comprise a quality factor of the one or more magnetostrictive resonators.

According to another aspect, a method may comprise applying an input signal to a first channel including a magnetostrictive resonator, the first channel having a first impedance, applying the input signal to a second channel having a second impedance, wherein the second impedance differs from the first impedance by a magnetostrictive resonator impedance, generating a combined output signal in response to output signals measured from both the first and second channels, and determining a resonance behavior of the magnetostrictive resonator in response to the combined output signal.

In some embodiments, applying the input signal to the first channel and applying the input signal to the second channel may be performed simultaneously. Generating the combined output signal may comprise subtracting a second channel output signal from a first channel output signal. In other embodiments, generating the combined output signal may comprise calculating a ratio between a first channel output signal from a second channel output signal.

According to yet another aspect, a method may comprise applying a stepped electrical signal to one or more driving coils to generate a first time-varying magnetic field, measuring a decaying electrical signal from one or more pick-up coils, wherein the one or more pick-up coils receive a second time-varying magnetic field generated by a plurality of magnetostrictive resonators in response to the first time-varying magnetic field, and determining a resonance frequency of each of the plurality of magnetostrictive resonators using a Fast Fourier Transform of the decaying electrical signal.

In some embodiments, applying the stepped electrical signal to one or more driving coils may comprise applying an electrical pulse having a width that is smaller than each period corresponding to the resonance frequencies of the plurality of magnetostrictive resonators. In other embodiments, measuring the decaying electrical signal from one or more pick-up coils may comprise using first and second pick-up coils that are wound in opposite directions.

BRIEF DESCRIPTION OF THE DRAWINGS

The invention described herein is illustrated by way of example and not by way of limitation in the accompanying drawings. For simplicity and clarity of illustration, elements illustrated in the drawings are not necessarily drawn to scale. For example, the dimensions of some elements may be exaggerated relative to other elements for clarity.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and appended claims.

In the following description, numerous specific details, such as types and interrelationships of system components, are set forth in order to provide a more thorough understanding of the present disclosure. It will be appreciated, however, by one skilled in the art that embodiments of the disclosure may be practiced without such specific details. In other instances, control structures, gate level circuits, and full software instruction sequences have not been shown in detail in order not to obscure the invention. Those of ordinary skill in the art, with the included descriptions, will be able to implement appropriate functionality without undue experimentation.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may be implemented as instructions carried by or stored on one or more machine-readable media, which may be read and executed by one or more processors. A machine-readable medium may be embodied as any device, mechanism, or physical structure for storing or transmitting information in a form readable by a machine (e.g., a computing device). For example, a machine-readable medium may be embodied as read only memory (ROM), random access memory (RAM), magnetic disk storage media, optical storage media, flash memory devices, electrical signals, and others.

In the drawings, specific arrangements or orderings of schematic elements, such as those representing devices, modules, components, and signals, may be shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements (e.g., solid or dashed lines or arrows) are used to illustrate a connection, relationship, or association between or among two or more schematic elements, the absence of any such connecting elements is not meant to imply that no connection, relationship or association can exist. In other words, some connections, relationships or associations between elements may not be shown in the drawings so as not to obscure the disclosure. In addition, for ease of illustration, a single connecting element may be used to represent multiple connections, relationships, or associations between elements. For example, where a connecting element represents a communication of signals, data, or instructions, it should be understood by those skilled in the art that such element may represent one or multiple signal paths, as may be needed, to effect the communication.

The present disclosure relates to systems for characterizing the resonance behavior of magnetostrictive resonators. For instance, the presently disclosed systems may be used to determine a resonance frequency and/or a quality factor (Q factor) for a magnetostrictive resonator. The presently disclosed systems may also be used to determine resonance frequencies and/or Q factors for a plurality of magnetostrictive resonators simultaneously. As described further below, these systems may use frequency domain techniques and/or time domain techniques to determine resonance behaviors. Where the magnetostrictive resonator(s) are each coupled to a sensing element that reacts with a target species in a sample (thus, acting as the sensing platform(s) of a biosensor system), the presently disclosed systems may provide portable, low-cost interrogation systems for the magnetostrictive resonator(s). By way of illustrative example, these interrogations systems might be incorporated into a handheld detection device for food safety.

Figure 1:
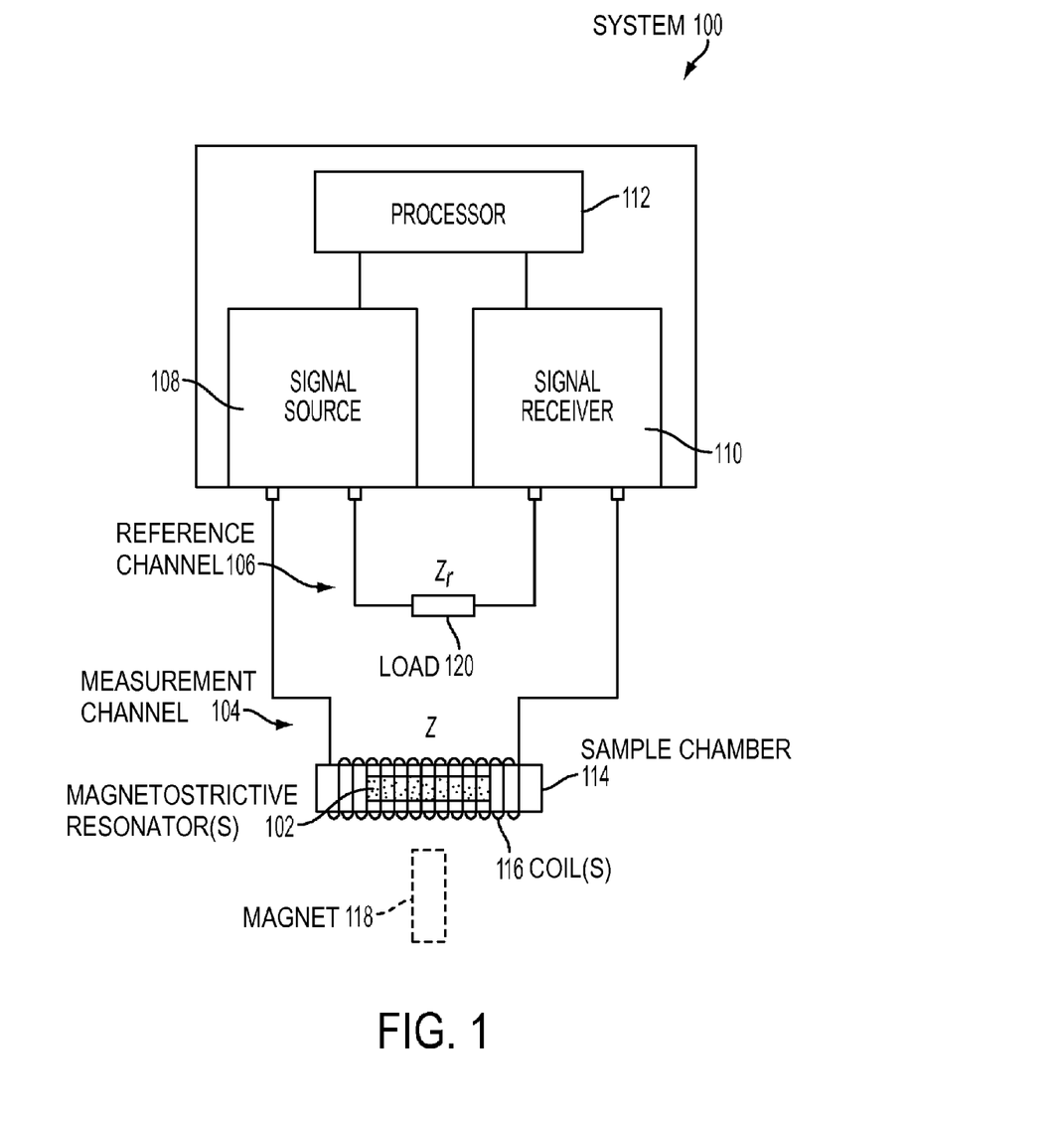
FIG. 1 is a simplified block diagram of one embodiment of a system for characterizing the resonance behavior of one or more magnetostrictive resonators using a frequency domain technique.

Referring now to FIG. 1, one illustrative embodiment of a system 100 for characterizing the resonance behavior of one or more magnetostrictive resonators 102 using a frequency domain technique is shown as a simplified block diagram. The system 100 includes a measurement channel 104, a reference channel 106, a signal source 108, a signal receiver 110, and a processor 112. In the illustrative embodiment of FIG. 1, the measurement channel 104 and the reference channel 106 are each communicatively coupled between the signal source 108 and the signal receiver 110. In the illustrative embodiment, the system 100 is embodied as a biosensor system for detecting and/or monitoring the presence of one or more biological species in a sample disposed in (or flowing through) a sample chamber 114. In some embodiments, the components of the system 100 may be contained in a handheld detection device. In other embodiments, however, one or more components of the system 100 (e.g., the processor 112) may be separate or remote from the remaining components of the system 100. It should also be appreciated that the system 100 may include other components, sub-components, and devices commonly found in electronic devices, which are not illustrated in FIG. 1 for clarity of the description.

The measurement channel 104 of the system 100 includes one or more coils 116 and one or more magnetostrictive resonators 102. It is contemplated that the one or more magnetostrictive resonators 102 may comprise any number of magnetostrictive resonators 102 of any desired size and composition (including a plurality of magnetostrictive resonators 102, possibly of varying size and composition). By way of illustrative example, the one or more magnetostrictive resonators 102 may comprise Metglas allow 2826 MB ribbon, commercially available from Honeywell International of Conway, S.C. As discussed above, each of the magnetostrictive resonators 102 may include a sensing element that reacts with a target species in a sample. The one or more coils 116 may include one or more driving coils (that generate magnetic fields), one or more pick-up coils (that receive magnetic fields generated by the one or more magnetostrictive resonators 102), and/or one or more coils that function as both a driving coil and a pick-up coil. In some embodiments, the one or more coils 116 may surround a portion of a sample and the one or more magnetostrictive resonators 102 may be disposed in the portion of the sample. In the illustrative embodiment of FIG. 1, the one or more coils 116 are wrapped around a portion of the sample chamber 114 enclosing a portion of the sample that includes the one or more magnetostrictive resonators 102.

The measurement channel 104 also includes a number of signal paths that communicatively couple the one or more coils 116 to both the signal source 108 and the signal receiver 110. The measurement channel 104 may optionally include one or more linear elements electrically coupled to the one or more coils 116 to enhance the output signal of the measurement channel 104 (as further described below). The measurement channel 104 may optionally include a magnet 118 (shown in phantom) to provide a constant bias to the one or more magnetostrictive resonators 102.

Figure 2:
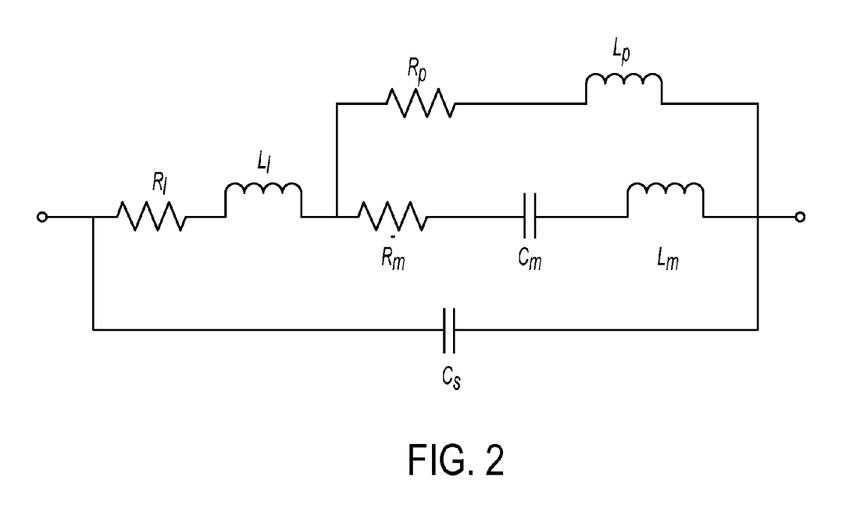
FIG. 2 illustrates one embodiment of an equivalent circuit model for a vibrating magnetostrictive resonator in one or more coils of the system of FIG. 1.

The measurement channel 104 has an overall impedance (Z) that includes impedances attributable to the one or more coils 116, to the one or more magnetostrictive resonators 102, and to the signal paths (as well as any other optional components included in the measurement channel 104). During operation of the system 100, a magnetostrictive resonator 102 vibrating in the one or more coils 116 may be modeled as an RLC oscillation circuit, as illustrated in FIG. 2. In this illustrative model, $C_s$ represents capacitance of the one or more coils 116; $R_p$ and $L_p$ represent resistance and inductance due to the presence the magnetostrictive resonator 102; $R_m$, $L_m$, and $C_m$ represent resistance, inductance, and capacitance due to the vibration of the magnetostrictive resonator 102; and $R_l$ and $L_l$ represent leaking resistance and inductance due to media (i.e., the sample) surrounding the magnetostrictive resonator 102 in the sample chamber 114.

Like the measurement channel 104, the reference channel 106 includes a number of signal paths that communicatively couple a load 120 to both the signal source 108 and the signal receiver 110. The reference channel 106 has an overall impedance ($Z_r$) that differs from the overall impedance, $Z$, of the measurement channel 104 by the impedance attributable to the one or more magnetostrictive resonators 102. In other words, the reference channel 106 has similar electrical characteristics to the measurement channel 104 but does not include any magnetostrictive resonators 102 (and, therefore, the impedance, $Z_r$, of the reference channel 106 does not include a magnetostrictive resonator impedance). In some embodiments, the reference channel 106 may have a similar configuration to the measurement channel 104, with the exception of the one or more magnetostrictive resonators 102. In such embodiments, the reference channel 106 may include one or more coils that surround a portion of the sample (within the sample chamber 114 or otherwise) that does not include the one or more magnetostrictive resonators 102. In other embodiments, however, the reference channel 106 need not interact with the sample; instead, the load 120 of the reference channel 106 may be designed to mimic the electrical characteristics of the measurement channel 104 without the one or magnetostrictive resonators 102.

The signal source 108 of the system 100 is configured to apply an input signal to both the measurement channel 104 and the reference channel 106. The signal source 108 may be embodied as any type of circuitry capable of generating a suitable input signal. In the illustrative embodiment, the signal source 108 comprises an AD9959 Direct Digital Synthesizer, commercially available from Analog Devices of Norwood, Mass. The signal source 108 may apply the input signal to both the measurement channel 104 and the reference channel 106 simultaneously. The input signal applied by the signal source 108 may be any suitable time-varying electrical signal, including, but not limited to, alternating current (AC) signals, with or without direct current (DC) offsets. In the illustrative embodiment, the signal source 108 applies an AC signal to the measurement channel 104 and the reference channel 106 and sweeps the AC signal over a range of frequencies that includes a resonance frequency of the one or more magnetostrictive resonators 102.

The signal receiver 110 of the system 100 is configured to measure output signals from both the measurement channel 104 and the reference channel 106 and to generate a combined output signal in response to the measured output signals. The signal receiver 110 may be embodied as any type of circuitry capable of measuring and processing output signals from the measurement channel 104 and the reference channel 106. In some embodiments, the signal source 108 and the signal receiver 110 may be embodied as circuitry on a single chip or board. In the illustrative embodiment, the signal receiver 110 comprises an AD8302 Gain Phase Detector, commercially available from Analog Devices of Norwood, Mass. When the input signal is applied to the measurement channel 104 and the reference channel 106 by the signal source 108 (as described above), the measurement channel 104 and the reference channel 106 each generate an output signal that may be measured by the signal receiver 110. In the illustrative embodiment, where the input signal is an AC signal, the output signals of the measurement channel 104 and the reference channel 106 will be varying potential signals, which may be expressed as $U_1 = I \cdot Z$ and $U_2 = I \cdot Z_r$, respectively.

Using the measured output signals, $U_1$ and $U_2$, the signal receiver 110 generates a combined output signal that reflects the impedance that is attributable to the one or more magnetostrictive resonators 102 of the system 100. Because the same input signal is applied to both the measurement channel 104 and the reference channel 106, differences between the measured output signals, $U_1$ and $U_2$, relate to differences between the impedance, Z, of the measurement channel 104 and the impedance, $Z_r$, of the reference channel 106 (i.e., the magnetostrictive resonator impedance). Using the relationships set forth above, Z may be expressed as:

$$Z = Z_r \frac{U_1}{U_2} = Z_r \frac{|U_1| e^{j(\omega t + \phi_1)}}{|U_2| e^{j(\omega t + \phi_2)}} = Z_r \left| \frac{U_1}{U_2} \right| e^{j(\phi_1 - \phi_2)},$$

where $\phi_1$ and $\phi_2$ are the phases of the measured output signals, $U_1$ and $U_2$, respectively. Thus, the impedance, Z, of the measurement channel 104 may determined by calculating the gain and the phase difference between the measured output signals, $U_1$ and $U_2$.

Figure 3A:
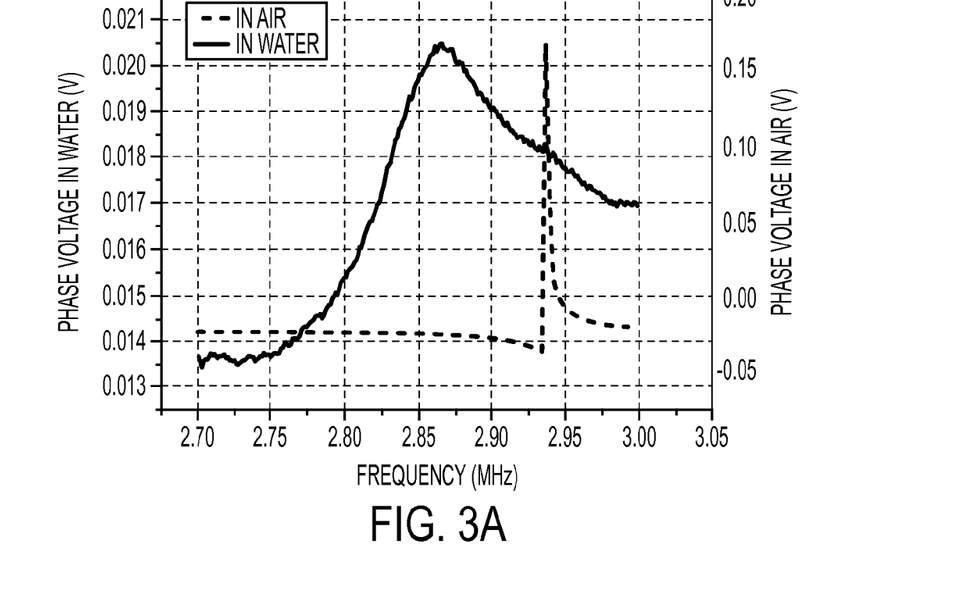
FIG. 3A is a plot of one example of a combined output signal generated by a signal receiver of the system of FIG. 1.
Figure 3B:
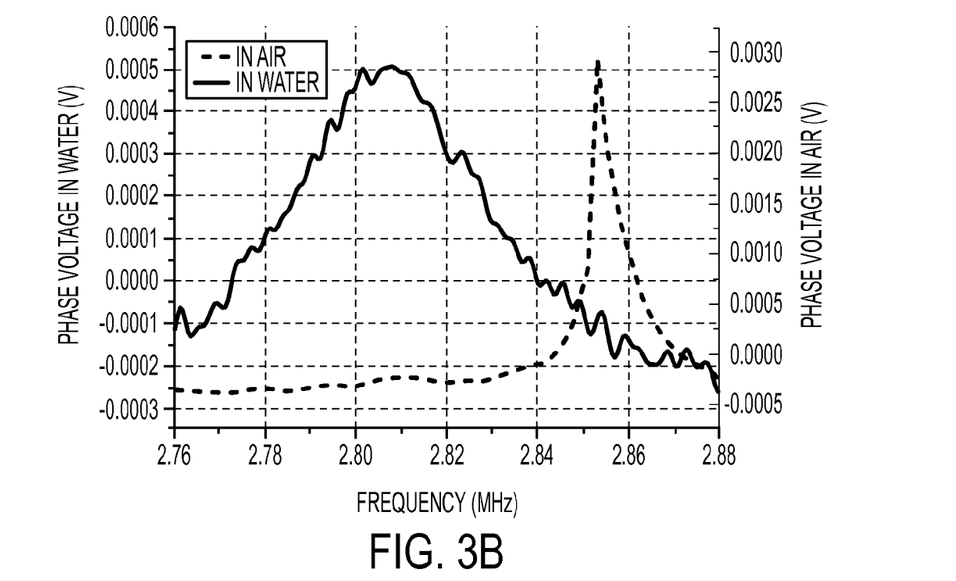
FIG. 3B is a plot of another example of a combined output signal generated by the signal receiver of the system of FIG. 1.

In some embodiments, the signal receiver 110 may generate a combined output signal by calculating a ratio between the measured output signals, $U_1$ and $U_2$. In other embodiments, the signal receiver 110 may generate a combined output signal by subtracting the measured output signal, $U_2$, of the reference channel 106 from the measured output signal, $U_1$, of the measurement channel 104. In still other embodiments, the signal receiver 110 may generate both a combined output signal that is a ratio between the measured output signals and a combined output signal that is a difference between the measured output signals. These combined output signals will be complex signals (i.e., signals including real and imaginary parts, or amplitude and phase components). The plots in FIGS. 3A-B are two illustrative examples of combined output signals generated by the signal receiver 110. The combined output signals illustrated in FIGS. 3A-B are ratios of a measured output signal, $U_1$, of the measurement channel 104 to a measured output signal, $U_2$, of the reference channel 106, for samples with either water and air as a medium, using a magnetostrictive resonator 102 with a length of 750 μm.

The processor 112 of the system 100 is configured to determine a resonance behavior of the one or more magnetostrictive resonators 102 in response to the combined output signal generated by the signal receiver 110. The processor 112 may be any type of processor capable of executing software/firmware, such as a microprocessor, digital signal processor, microcontroller, or the like. As shown in FIG. 1, the processor 112 is communicatively coupled to both the signal source 108 and the signal receiver 110 via a number of signal paths. In some embodiments, the processor 112 may reside on the same chip or board as the signal source 108 and/or the signal receiver 110. In other embodiments, the processor 112 may be separate or remote from the remaining components of the system 100 and may communicate with the signal source 108 and the signal receiver 110 via a communications interface (not shown). In such embodiments, the processor 112 may be embodied in a personal computer, a workstation, a laptop computer, a handheld computer, or other computing device.

The processor 112 may use one or more combined output signals received from the signal receiver 110 (such as those illustrated in FIGS. 3A-B) to determine a resonance behavior, such as a resonance frequency or a Q factor, of the one or more magnetostrictive resonators 102. Where the system 100 includes a plurality of magnetostrictive resonators 102, the processor 112 may determine one or more resonance behaviors for each of the plurality of magnetostrictive resonators 102 (or for a subset thereof). The processor 112 may analyze the frequency dependence of the real and imaginary parts, or of the amplitude and phase, of a combined output signal to determine the desired resonance behavior(s). In some embodiments, the processor 112 may also be configured to supply commands to the signal source 108 regarding the characteristics of the input signal to be applied.

Figure 4:
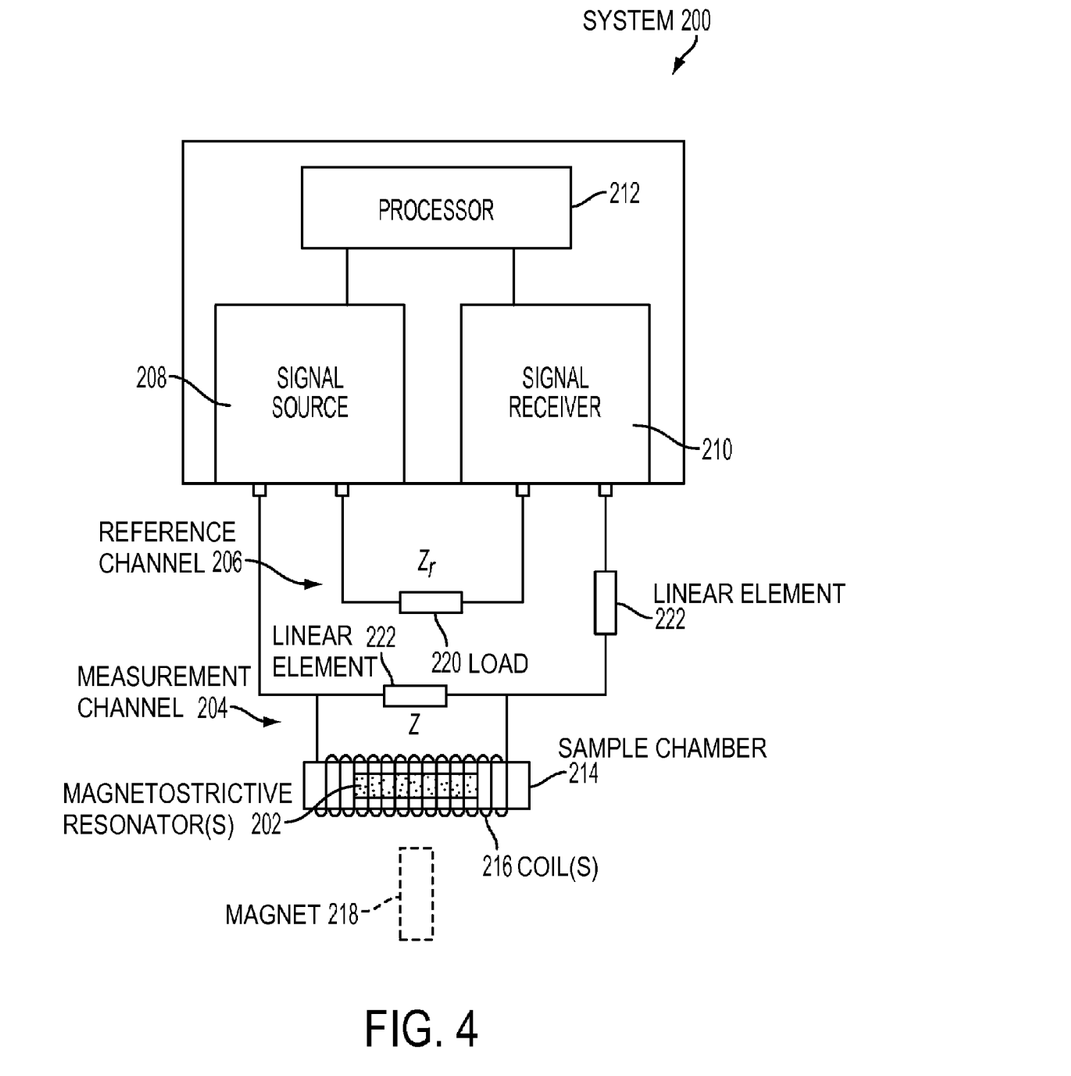
FIG. 4 is a simplified block diagram of another embodiment of a system for characterizing the resonance behavior of one or more magnetostrictive resonators using a frequency domain technique.
Figure 5A:
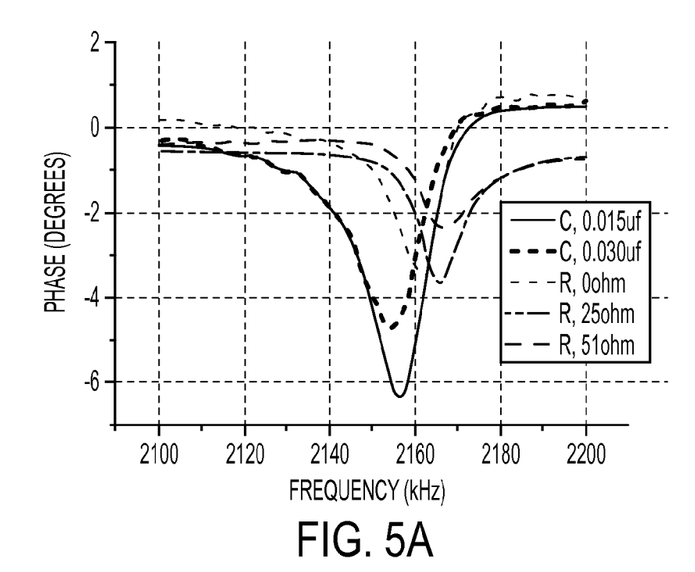
FIG. 5A is a plot illustrating the effect on a combined output signal of various capacitors and resistors when electrically coupled in series with one or more coils of the system of FIG. 4.
Figure 5B:
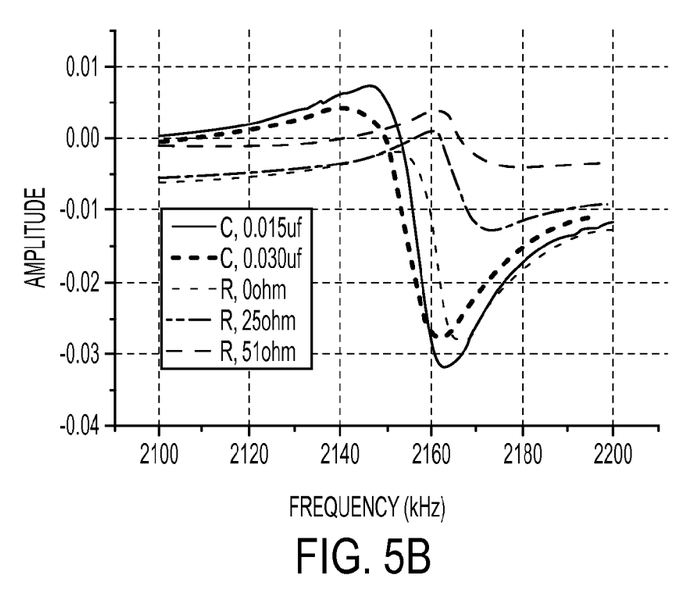
FIG. 5B is a plot illustrating the effect on another combined output signal of various capacitors and resistors when electrically coupled in series with one or more coils of the system of FIG. 4.

Referring now to FIG. 4, another illustrative embodiment of a system 200 for characterizing the resonance behavior of one or more magnetostrictive resonators 202 using a frequency domain technique is shown as a simplified block diagram. The system 200 includes similar components to those of the system 100 (shown in FIG. 1 and described in detail above). As shown in FIG. 4, the system 200 further comprises a number of linear elements 222 electrically coupled to the one or more coils 216 of the measurement channel 204 to enhance the output signal of the measurement channel 204. These linear elements 222 may each be embodied as one or more resistors, capacitors, and/or inductors. The linear elements 222 may be electrically coupled in series and/or in parallel with the one or more coils 216 of the measurement channel 204. Although not shown in FIG. 4, it is also contemplated that a number of linear elements 222 may be electrically coupled (in series and/or in parallel) to the load 220 of the reference channel 206 to enhance the output signal of the reference channel 206. The plots of FIGS. 5A-B each illustrate the effect on a combined output signal of various capacitors/resistors 222 when electrically coupled in series with the one or more coils 216 of the measurement channel 204.

Figure 6:
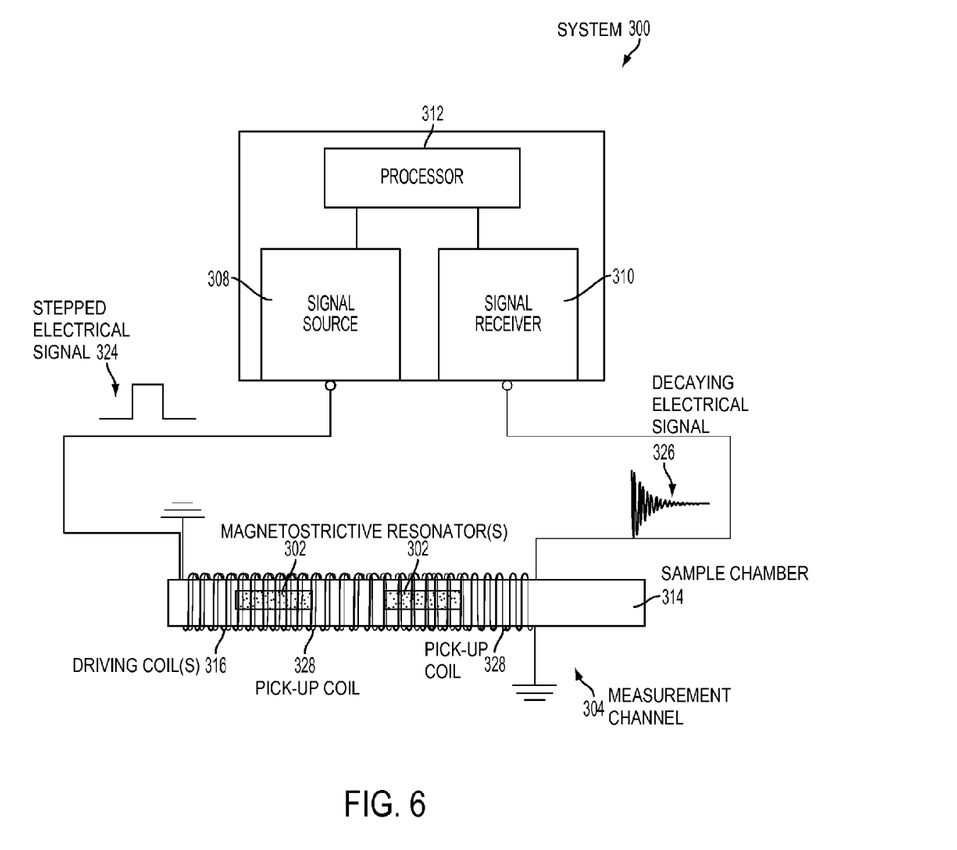
FIG. 6 is a simplified block diagram of one embodiment of a system for characterizing the resonance behavior of one or more magnetostrictive resonators using a time domain technique.

Referring now to FIG. 6, one illustrative embodiment of a system 300 for characterizing the resonance behavior of one or more magnetostrictive resonators 302 using a time domain technique is shown as a simplified block diagram. The system 300 includes a measurement channel 304, a signal source 308, a signal receiver 310, a processor 312, and a sample chamber 314. Except as noted below, these components may be similar to the corresponding components of the system 100 (shown in FIG. 1 and described in detail above). In the illustrative embodiment, the system 300 is embodied as a biosensor system for detecting and/or monitoring the presence of one or more biological species in a sample disposed in (or flowing through) the sample chamber 314. In some embodiments, the components of the system 300 may be contained in a handheld detection device. In other embodiments, however, one or more components of the system 300 (e.g., the processor 312) may be separate or remote from the remaining components of the system 300. It should also be appreciated that the system 300 may include other components, sub-components, and devices commonly found in electronic devices, which are not illustrated in FIG. 6 for clarity of the description.

The measurement channel 304 of the system 300 includes one or more driving coils 316, one or more pick-up coils 328, and one or more magnetostrictive resonators 302. Although a plurality of magnetostrictive resonators 302 are illustrated in FIG. 6, it is contemplated that the system 300 may be used with any number of magnetostrictive resonators 302 of any desired size and composition (including a plurality of magnetostrictive resonators 302 of varying size and composition). As discussed above, each of the magnetostrictive resonators 302 may include a sensing element that reacts with a target species in a sample. The measurement channel 104 also includes a number of signal paths that communicatively couple the one or more driving coils 316 to the signal source 308 and a number of signal paths that communicatively couple the one or more pick-up coils 328 to the signal receiver 310. In the illustrative embodiment of FIG. 6, the system 300 includes two pick-up coils 328 with the same number of windings, but wound in opposite directions. This configuration may reduce the influence of a magnetic field generated by the one or more driving coils 316 on measurements made by the pick-up coils 328 by increasing the signal-to-noise ratio.

Figure 7A:
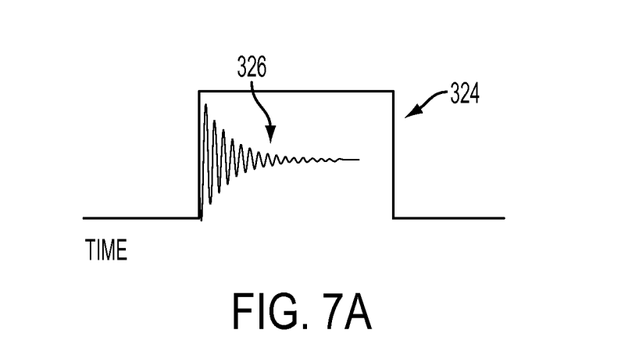
FIG. 7A illustrates the measurement of a decaying electrical signal after the rising step of a stepped electrical signal of longer duration.
Figure 7B:
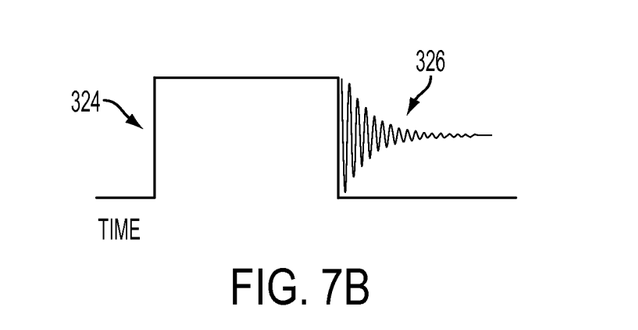
FIG. 7B illustrates the measurement of a decaying electrical signal after the falling step of a stepped electrical signal of longer duration.
Figure 7C:
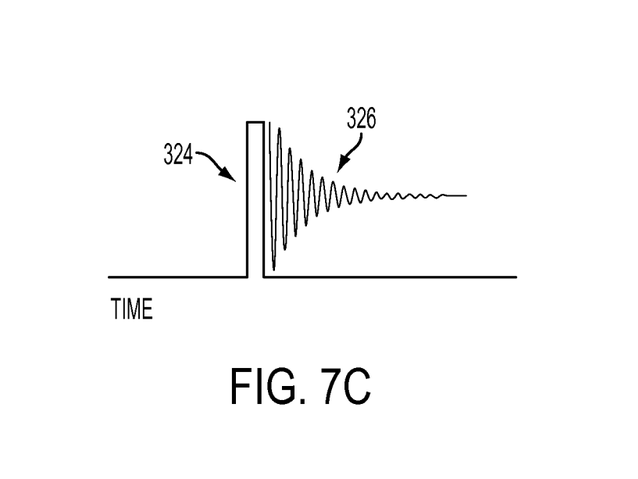
FIG. 7C illustrates the measurement of a decaying electrical signal after a stepped electrical signal of shorter duration.

The signal source 308 of the system 300 is configured to apply a stepped electrical signal 324 to the one or more driving coils 316 (of the measurement channel 304). The signal source 108 may be embodied as any type of circuitry capable of generating a stepped electrical signal 324 of any suitable duration. For instance, in some embodiments, the stepped electrical signal 324 may be an electrical pulse 324 having a width that is smaller than the periods corresponding to the resonance frequencies of the plurality of magnetostrictive resonators 302, as shown in FIG. 7C. When the stepped electrical signal 324 is applied, the one or more driving coils 316 will generate a time-varying magnetic field. This time-varying magnetic field will cause the plurality of magnetostrictive resonators 302 to vibrate. The vibrations of the plurality of magnetostrictive resonators 302 will, in turn, create a responsive time-varying magnetic field that will be received by the one or more pick-up coils 328 of the measurement channel 304.

The signal receiver 310 of the system 300 is configured to measure a decaying electrical signal 326 from the one or more pick-up coils 328. When the one or more pick-up coils 328 receive the responsive time-varying magnetic field generated by the plurality of magnetostrictive resonators 302, a decaying electrical signal 326 will be generated by the one or more pick-up coils 328. In some embodiments, the decaying electrical signal 326 may be an exponentially decaying sinusoidal signal (as illustrated in FIGS. 6 and 7A-C). The signal receiver 310 may be embodied as any type of circuitry capable of measuring the decaying electrical signal 326 from the one or more pick-up coils 328. In some embodiments, the signal source 308 and the signal receiver 310 may be embodied as circuitry on a single chip or board. Where the stepped electrical signal 324 is of longer duration, the decaying electrical signal 326 may be measured after the rising step of the stepped electrical signal 324 (as shown in FIG. 7A) and/or the falling step of the stepped electrical signal 324 (as shown in FIG. 7B). In embodiments employing an electrical pulse 324 (i.e., a stepped electrical signal 324 of shorter duration), the decaying electrical signal 326 may be measured after the electrical pulse 324 (as shown in FIG. 7C). After measuring the decaying electrical signal 326, the signal receiver 310 may transmit the decaying electrical signal 326, or information regarding the decaying electrical signal 326, to the processor 312.

The processor 312 of the system 300 is configured to determine a resonance frequency of each of the plurality of magnetostrictive resonators 302 using a Fast Fourier Transform (FFT) of the decaying electrical signal 326. The processor 312 may be any type of processor capable of executing software/firmware, such as a microprocessor, digital signal processor, microcontroller, or the like. As shown in FIG. 6, the processor 312 is communicatively coupled to both the signal source 308 and the signal receiver 310 via a number of signal paths. In some embodiments, the processor 312 may reside on the same chip or board as the signal source 308 and/or the signal receiver 310. In other embodiments, the processor 312 may be separate or remote from the remaining components of the system 300 and may communicate with the signal source 308 and the signal receiver 310 via a communications interface (not shown). In such embodiments, the processor 312 may be embodied in a personal computer, a workstation, a laptop computer, a handheld computer, or other computing device.

Figure 8A:
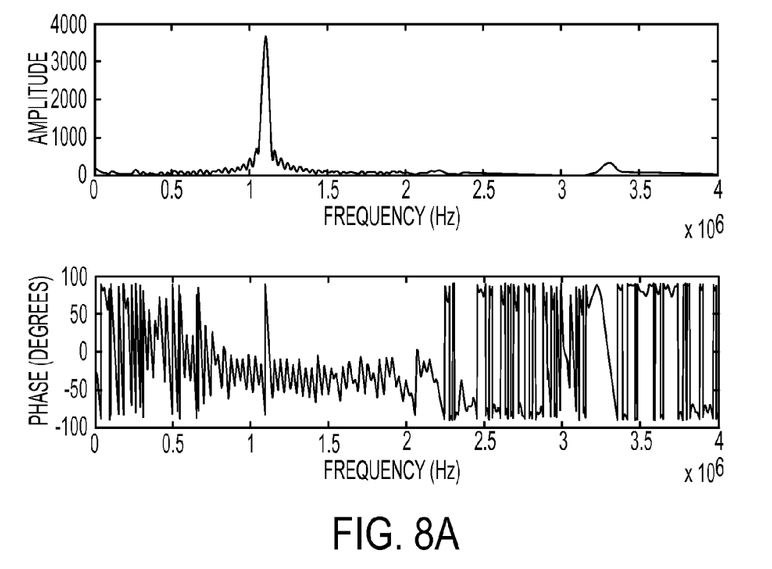
FIG. 8A illustrates the Fast Fourier Transform (FFT) of a decaying electrical signal as plots of amplitude and phase versus frequency.
Figure 8B:
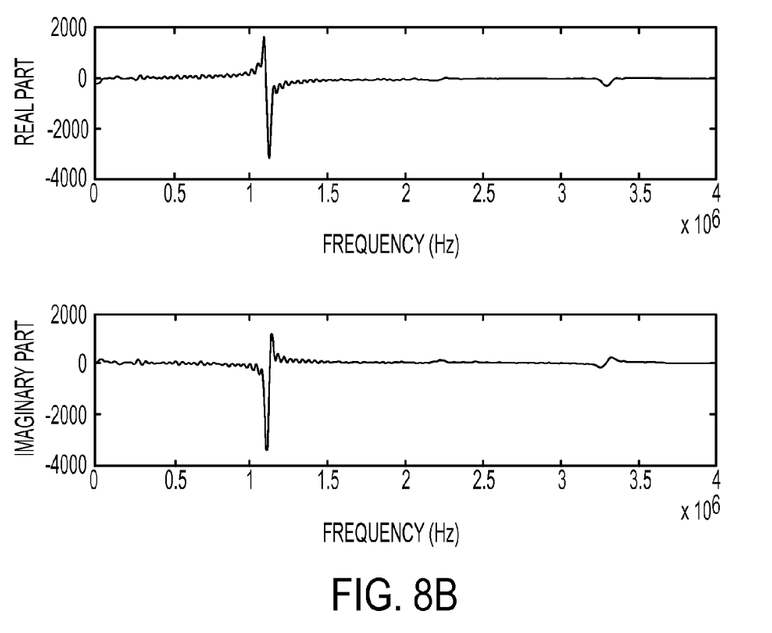
FIG. 8B illustrates the FFT of a decaying electrical signal as plots of the real and imaginary parts versus frequency.
Figure 9A:
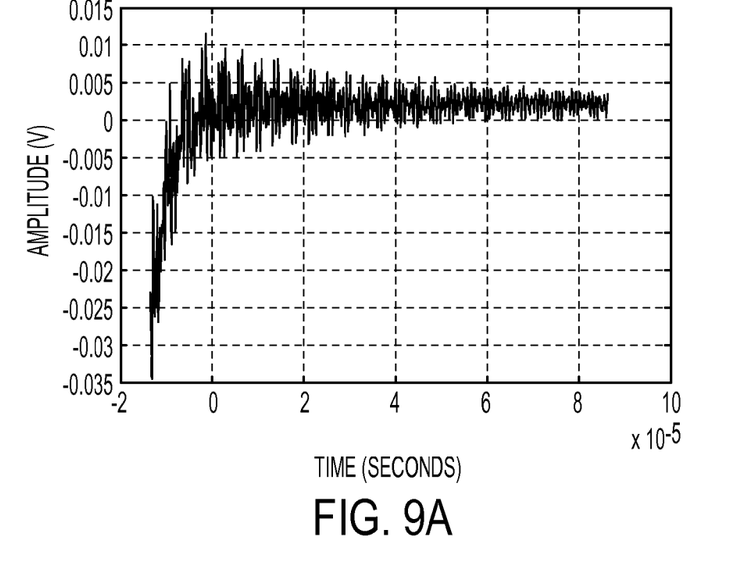
FIG. 9A is a plot of one example of a decaying electrical signal resulting from three magnetostrictive resonators of different sizes.
Figure 9B:
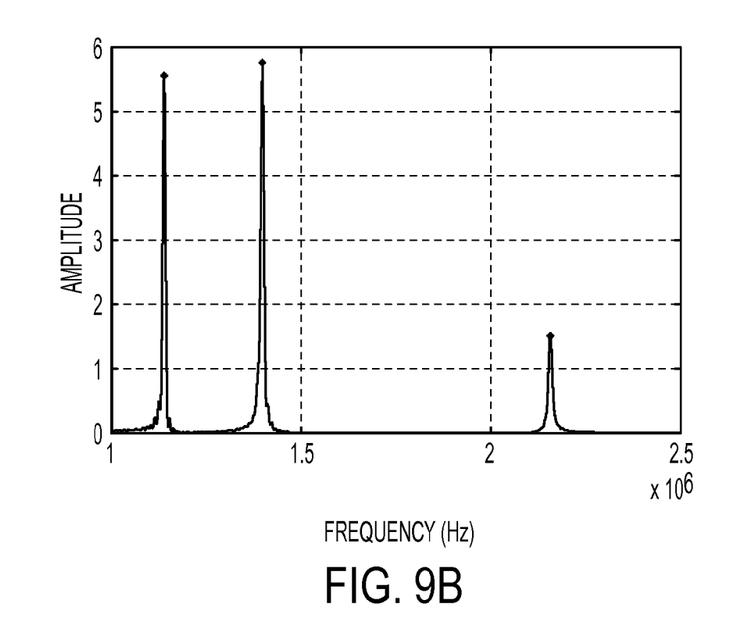
FIG. 9B is a plot of the FFT of the decaying electrical signal of FIG. 9A.

After receiving the decaying electrical signal 326 (or information regarding the decaying electrical signal 326) from the signal receiver 310, the processor 312 applies an FFT to transform the decaying electrical signal 326 from the time-domain to the frequency domain. Using the FFT, the processor 312 may derive plots of amplitude and phase versus frequency (as shown in FIG. 8A) or plots of the real and imaginary parts of the decaying electrical signal 326 versus frequency (as shown in FIG. 8B). As can be seen in FIGS. 8A-B, the resonance frequency of a magnetostrictive resonator 302 may readily be determined from these plots. In the illustrative embodiment, the processor 312 is configured to simultaneously determine the resonance frequency of each of the plurality of magnetostrictive resonators 302. One illustrative example of a decaying electrical signal 326 where the system 300 includes three magnetostrictive resonators 302 of different sizes is shown in FIG. 9A. After receiving the decaying electrical signal 326 of FIG. 9A from the signal receiver 310, the processor 312 may use an FFT of the decaying electrical signal 326 to obtain the plot shown in FIG. 9B. The processor 312 may then locate the three peaks in this data to determine the three resonance frequencies of the three magnetostrictive resonators 302. In some embodiments, the processor 312 may also be configured to supply commands to the signal source 308 regarding the characteristics of the stepped electrical signal 324 to be applied.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the systems, apparatus, and methods described herein. It will be noted that alternative embodiments of the systems, apparatus, and methods of the present disclosure may not include all of the features described yet still benefit from at least some of the advantages of such features. Those of ordinary skill in the art may readily devise their own implementations of systems, apparatus, and methods that incorporate one or more of the features of the present invention and fall within the spirit and scope of the present disclosure.

The invention claimed is:

1. Apparatus configured to characterize a resonance behavior of one or more magnetostrictive and/or magnetoelastic resonators, the apparatus comprising:
   a first channel including one or more coils and the one or more magnetostrictive and/or magnetoelastic resonators, the first channel having a first impedance;
   a second channel having a second impedance different from the first impedance, the difference between the first and second impedances being attributable to the one or more magnetostrictive and/or magnetoelastic resonators of the first channel;
   a signal source coupled to the first channel and to the second channel, the signal source being configured to apply an input signal to both the first and second channels;
   a signal receiver coupled to the first channel and to the second channel, the signal source being configured to generate a combined output signal in response to output signals measured from both the first and second channels; and
   a processor coupled to the signal receiver and configured to (i) determine the resonance behavior of the one or more magnetostrictive and/or magnetoelastic resonators in response to the combined output signal and (ii) output a value indicative of the resonance behavior of the one or more magnetostrictive and/or magnetoelastic resonators as the resonance characterization.

2. The apparatus of claim 1, wherein the one or more magnetostrictive and/or magnetoelastic resonators comprise a plurality of magnetostrictive and/or magnetoelastic resonators.

3. The apparatus of claim 1, wherein the one or more coils surround a first portion of a sample and the one or more magnetostrictive and/or magnetoelastic resonators are disposed in the first portion of the sample.

4. The apparatus of claim 3, wherein the one or more magnetostrictive and/or magnetoelastic resonators each comprise a sensing element that reacts with a target species in the sample.

5. The apparatus of claim 3, wherein the second channel includes one or more coils surrounding a second portion of the sample and no magnetostrictive and/or magnetoelastic resonators are disposed in the second portion of the sample.

6. The apparatus of claim 5, wherein the second channel further includes a linear element electrically coupled to the one or more coils of the second channel.

7. The apparatus of claim 1, wherein the first channel further includes a linear element electrically coupled to the one or more coils of the first channel.

8. The apparatus of claim 1, wherein the signal source is configured to sweep the input signal over a range of frequencies including a resonance frequency of the one or more magnetostrictive and/or magnetoelastic resonators.

9. The apparatus of claim 1, wherein the combined output signal is a difference between the output signals measured from both the first and second channels.

10. The apparatus of claim 1, wherein the combined output signal is a ratio between the output signals measured from both the first and second channels.

11. The apparatus of claim 1, wherein the resonance behavior of the one or more magnetostrictive and/or magnetoelastic resonators comprises a resonance frequency of the one or more magnetostrictive and/or magnetoelastic resonators.

12. The apparatus of claim 1, wherein the resonance behavior of the one or more magnetostrictive and/or magnetoelastic resonators comprises a quality factor of the one or more magnetostrictive and/or magnetoelastic resonators.

13. A method of W characterizing a resonance behavior of a magnetostrictive and/or magnetoelastic resonator, the method comprising: applying, using a signal source, an input signal to a first channel including the magnetostrictive and/or magnetoelastic resonator, the first channel having a first impedance; applying, using the signal source, the input signal to a second channel having a second impedance different from the first impedance, the difference between the first and second impedances being attributable to the magnetostrictive and/or magnetoelastic resonator of the first channel;
   generating, using a signal receiver, a combined output signal in response to output signals measured from both the first and second channels;
   determining, using a processor, the resonance behavior of the magnetostrictive and/or magnetoelastic resonator in response to the combined output signal; and
   outputting, using the processor, a value indicative of the resonance behavior of the magnetostrictive and/or magnetoelastic resonator as the resonance characterization.

14. The method of claim 13, wherein applying the input signal to the first channel and applying the input signal to the second channel are performed simultaneously by the signal source.

15. The method of claim 13, wherein generating the combined output signal comprises subtracting, using the signal receiver, a second channel output signal from a first channel output signal.

16. The method of claim 13, wherein generating the combined output signal comprises calculating, using the signal receiver, a ratio between a first channel output signal from a second channel output signal.

17. A method of characterizing resonance behavior of a plurality of magnetostrictive and/or magnetoelastic resonators, the method comprising:
   applying, using a signal source, a stepped electrical signal to one or more driving coils to generate a first time-varying magnetic field;
   measuring, using a signal receiver, a decaying electrical signal from one or more pick-up coils, wherein the one or more pick-up coils receive a second time-varying magnetic field generated by the plurality of magnetostrictive and/or magnetoelastic resonators in response to the first time-varying magnetic field;

determining, using a processor, a resonance frequency of each of the plurality of magnetostrictive and/or magnetoelastic resonators using a Fast Fourier Transform of the decaying electrical signal;

outputting, using the processor, one or more values indicative of the resonance frequency of each of the plurality of magnetostrictive and/or magnetoelastic resonators as the resonance characterization.

18. The method of claim 17, wherein applying the stepped electrical signal to one or more driving coils comprises applying, using the signal source, an electrical pulse having a width that is smaller than each period corresponding to the resonance frequencies of the plurality of magnetostrictive and/or magnetoelastic resonators.

19. The method of claim 17, wherein measuring the decaying electrical signal from one or more pick-up coils comprises measuring, using the signal receiver, the decaying electrical signal from first and second pick-up coils that are wound in opposite directions.

\* \* \* \* \*